United States Patent [19]

Yoon

[11] Patent Number: 5,620,452
[45] Date of Patent: Apr. 15, 1997

[54] SURGICAL CLIP WITH DUCTILE TISSUE PENETRATING MEMBERS

[76] Inventor: InBae Yoon, 2101 Highland Ridge Dr., Phoenix, Md. 21131

[21] Appl. No.: 361,823

[22] Filed: Dec. 22, 1994

[51] Int. Cl.⁶ ............................................. A61B 17/04
[52] U.S. Cl. ........................... 606/151; 606/157; 606/219
[58] Field of Search ..................... 606/151, 146, 606/147, 148, 142–143, 213, 219, 157, 158

[56] References Cited

U.S. PATENT DOCUMENTS

| | | | |
|---|---|---|---|
| 1,756,670 | 4/1930 | Treat | 606/151 |
| 3,134,152 | 5/1964 | Pei | 606/213 |
| 3,363,628 | 1/1968 | Wood . | |
| 3,856,016 | 12/1974 | Davis . | |
| 4,064,881 | 12/1977 | Meredith . | |
| 4,414,721 | 11/1983 | Hufnagel . | |
| 4,430,998 | 2/1984 | Harvey et al. | 606/216 |
| 4,476,865 | 10/1984 | Failla et al. . | |
| 4,548,201 | 10/1985 | Yoon . | |
| 4,794,927 | 1/1989 | Yoon . | |
| 4,967,949 | 11/1990 | Sandhaus | 227/176 |
| 5,015,249 | 5/1991 | Nakao et al. | 606/142 |
| 5,049,153 | 9/1991 | Nakao et al. | 606/151 |
| 5,100,418 | 3/1992 | Yoon et al. | 606/139 |
| 5,156,609 | 10/1992 | Nakao et al. | 606/142 |
| 5,171,250 | 12/1992 | Yoon . | |
| 5,171,253 | 12/1992 | Klieman | 606/158 |
| 5,201,746 | 4/1993 | Shichman | 606/151 |
| 5,219,353 | 6/1993 | Garvey, III et al. | 606/157 |
| 5,222,961 | 6/1993 | Nakao et al. | 606/143 |
| 5,366,458 | 11/1994 | Korthoff et al. | 606/151 |
| 5,366,459 | 11/1994 | Yoon | 606/151 |

FOREIGN PATENT DOCUMENTS 1389762  4/1988  U.S.S.R. .

*Primary Examiner*—Gary Jackson

[57] ABSTRACT

A surgical clip for constricting anatomical vessels and organs includes at least two generally opposed arms extending from opposite ends of a base member, a plurality of apertures formed in one of the arms and a plurality of ductile tissue penetrating members carried by the other arm in opposed relation to the apertures.

16 Claims, 4 Drawing Sheets

SURGICAL CLIP WITH DUCTILE TISSUE PENETRATING MEMBERS

BACKGROUND OF THE INVENTION

1. Field of the Invention

The present invention relates generally to surgical devices and, more particularly, to an improved surgical clip structure and method for constricting anatomical vessels and organs.

2. Description of the Prior Art

Surgical ligating clips are widely used to constrict or occlude anatomical tissue, such as tubular vessels and organs, during surgical procedures. The clips are generally U-shaped with opposed arms being positioned around anatomical tissue and clamped together in order to constrict the tissue. Instruments for applying surgical clips, commonly referred to as "clip appliers," can be configured for applying a single clip or multiple clips in series and can be adapted for use in both open and minimally invasive (i.e., endoscopic) surgical procedures.

Prior art surgical clips are commonly made of ductile metals, such as titanium, and are secured to tissue by squeezing or crimping opposed arms of the clip across the tissue after the clip has been properly positioned. Once crimped, the arms of a metal clip tend to remain crimped; however, metal clips will occasionally come off the tissue to which they have been applied when knocked by instruments moved about the operative field or, in the case of occluded vessels, the clips will loosen as a result of the vessels bulging.

Some metal clips also have a distal locking feature whereby distal ends of the opposed arms are configured to interlock; however, since central portions of the arms remain free to move, these clips will also tend to loosen over time when used to occlude vessels that bulge.

Other prior art surgical clips are made from materials that cannot maintain a deformed shape, such as certain bioabsorbable materials. These clips are secured around tissue by use of interlocking members carried on opposed arms of the clip. However, since the arms of these clips will not retain a crimped shape in the event that the interlocking members fail to engage, clips of this type will not function as desired when there is incomplete engagement of the interlocking members. Furthermore, the materials from which such clips are made can relax over time causing the clips to loosen, whereby, for example, a vessel lumen would cease to be effectively occluded.

SUMMARY OF THE INVENTION

Accordingly, it is a primary object of the present invention to overcome the above mentioned disadvantages of the prior art and to prevent loosening of a surgical clip having opposed arms clamped around a tubular vessel or organ by locking the arms together with ductile tissue penetrating members carried by one or both of the arms in opposed relation to apertures formed in the other arm.

Another object of the present invention is to apply a more uniform pressure across an occluded vessel or organ by use of a surgical clip having opposed arms locked together with plastically deformed tissue penetrating members passing through apertures in one or both of the arms.

A further object of the present invention is to prevent opposed arms of a surgical clip from sliding off a tubular vessel or organ by carrying ductile tissue penetrating members on one or both of the arms in opposed relation to apertures formed in the other arm and passing the ductile tissue penetrating members through the tubular vessel or organ.

Some of the advantages of the present invention over the prior art are that the surgical clip of the present invention applies a more uniform pressure across occluded vessels and organs, that the arms of the clip do not separate or loosen as readily over time, that the clip is not easily dislodged from occluded vessels and organs by inadvertent contact with medical instruments, that the arms and tissue penetrating members of the clip can be made of the same or different materials so that, for example, one can be bioabsorbable and the other non-bioabsorbable, and that the clip can be applied using conventional clip applying instruments in both open and closed or minimally invasive surgical procedures.

The present invention is generally characterized in a surgical clip including a base and at least two generally opposed arms extending from the base with a plurality of apertures formed in one or both of the arms and a plurality of ductile tissue penetrating members carried by one or both of the arms in opposed relation to the apertures.

Another aspect of the present invention is generally characterized in a method of constricting anatomical tissue, such as vessels and organs, including the steps of positioning the anatomical tissue between generally opposed coextensive arms of a ductile clip, bending the clip to move distal ends of the arms together, compressing the clip around the anatomical tissue, penetrating through the anatomical tissue with ductile tissue penetrating members carried by one or both of the arms, passing ends of the tissue penetrating members through apertures in the opposed arm until they protrude and shaping the protruding ends of the tissue penetrating members to bear against the opposed arm.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

Figure 1:
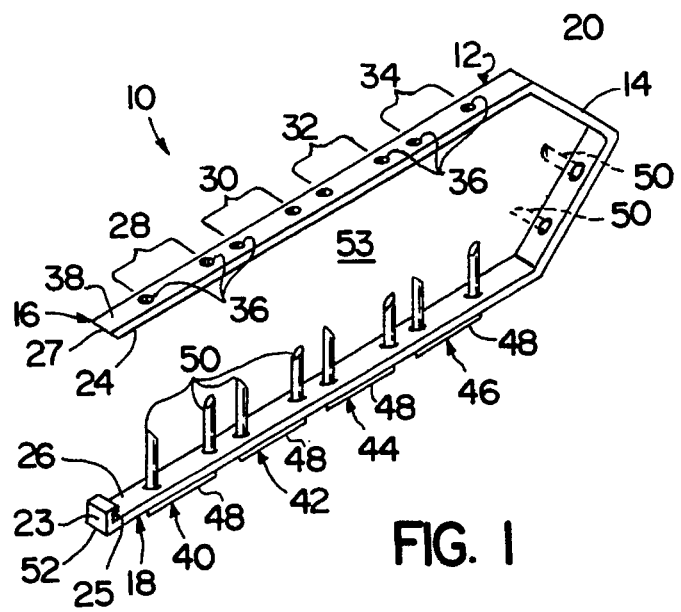
FIG. 1 is a perspective view of a surgical clip according to the present invention.

A surgical clip 10 according to the present invention, as illustrated in FIG. 1, includes a ductile strip 12 of medically-acceptable bioabsorbable or non-bioabsorbable material configured to form a V-shaped hinge or base 14 and a pair of generally opposed coextensive parallel arms 16 and 18 extending distally from opposite ends 20 and 22 of the base.

Arms 16 and 18 are generally rectangular in cross-section and define opposed tissue engaging inner faces 24 and 26. Lower arm 18 terminates distally at an inwardly turned portion or hook 23 having an inner latching surface 25 configured to mate with a tapered distal end 27 of upper arm 16 when the arms are clamped together.

Four pairs 28, 30, 32 and 34 of spaced openings or apertures 36 are formed through upper arm 16 along a longitudinal axis of the arm and extend from the inner face 24 of the arm to an outer face 38. Four staples 40, 42, 44 and 46, each having a cross member 48 and a pair of tissue penetrating legs 50 extending perpendicularly from opposed ends of the cross member, are arranged end-to-end on lower arm 18 with cross members 48 abutting an outer face 52 of the arm 18 and the tissue penetrating legs 50 extending through openings in the lower arm 18 toward the apertures 36 in upper arm 16. The legs of staples 40, 42, 44 and 46 are aligned with the first, second, third and fourth pairs of apertures 28, 30, 32 and 34 in upper arm 16, respectively, to facilitate passage of the legs through the apertures when arms 16 and 18 are clamped together.

Staples 40, 42, 44 and 46 can be made of any medically-acceptable material that is ductile, malleable or plastically deformable (that is, any material that when bent remains in the bent condition) including stainless steel, titanium, tantalum and other non-bioabsorbable and bioabsorbable metal and plastic materials. The staples are secured to leg 18 by friction fit, adhesive bonding or by any other suitable method of attachment.

Figure 2:
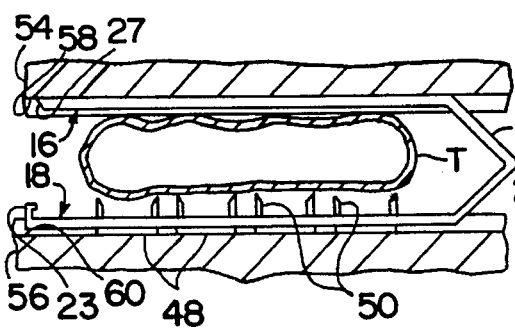
FIGS. 2–5 are side views, partly in section, illustrating use of the surgical clip of FIG. 1.

In use, the clip 10 is provided as shown in FIG. 1 with arms 16 and 18 extending in parallel from ends 20 and 22 of the V-shaped base 14 to define a tissue-receiving space 53 between the arms. The clip 10 can be manually positioned around tissue and compressed using forceps or, as shown in FIG. 2, arms 16 and 18 of the clip can be received in opposed jaws 54 and 56 of a conventional clip applying instrument of the type used for applying single or multiple clips to anatomical tissue during open or minimally-invasive surgical procedures. Exemplary of such clip applying instruments are the LIGACLIP applier from Ethicon Endo-Surgery of Cincinatti, Ohio, the ENDOCLIP applier from U.S. Surgical Corp. of Norwalk, Conn., or any of the clip appliers shown and described in U.S. Pat. Nos. 5,100,418 and 5,171,250 to Yoon; U.S. Pat. Nos. 5,084,057 and 5,100,420 to Green et al; U.S. Pat. No. 5,112,343 to Thornton; U.S. Pat. Nos. 5,171,247 to Hughett and 5,171,249 to Stefanchik et al; and U.S. Pat. No. 5,192,288 to Thompson et al.

When a clip applier is used, arms 16 and 18 are held within opposed channels or grooves 58 and 60 formed in the applicator jaws 54 and 56. The jaws 54 and 56 can be oriented parallel to a longitudinal axis of the clip applier, perpendicular to the longitudinal axis or at any other angle for applying the clips to anatomical tissue.

Figure 3:
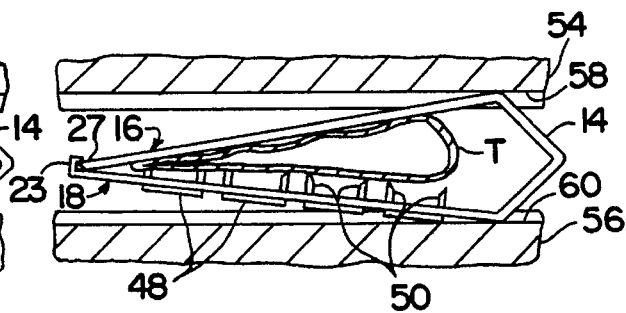
Figure 4:
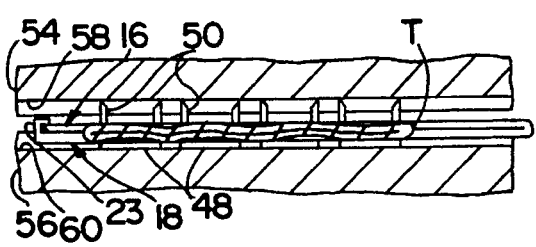
Figure 5:
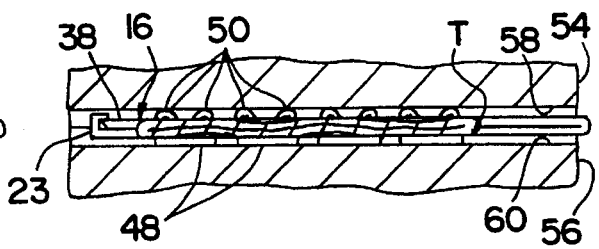
Figure 6:
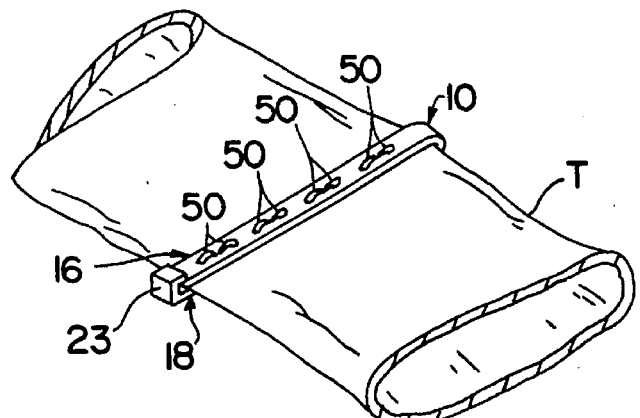
FIG. 6 is a perspective view of the surgical clip of FIG. 1 applied to anatomical tissue.

With clip 10 held between jaws 54 and 56 of the clip applier, anatomical tissue T, such as a tubular vessel or organ, is positioned within the tissue receiving space between arms 16 and 18, and the jaws 54 and 56 are closed together. Distal end 27 of upper arm 16 approaches hook 23 of lower arm 18 and mates with the hook to form a closed loop surrounding the tissue T as shown in FIG. 3. Further compression of the clip 10 causes staple legs 50 to penetrate through the anatomical tissue T and to be received within apertures 36 in upper arm 16 as shown in FIG. 4. The sharp tissue penetrating tips of the staple legs 50 protrude from the apertures 36 and are bent against the upper jaw 54 to engage the outer face 38 of upper arm 16 as shown in FIG. 5. The legs 50 will remain in the bent condition as a result of their being plastically shaped or deformed and will thus hold the arms of the clip together while applying a uniform pressure across the occluded tissue. With the staple legs 50 properly formed, jaws 54 and 56 can be opened and moved away from the tissue T leaving the clip 10 securely clamped around the tissue T as shown in FIG. 6.

Figure 7A:
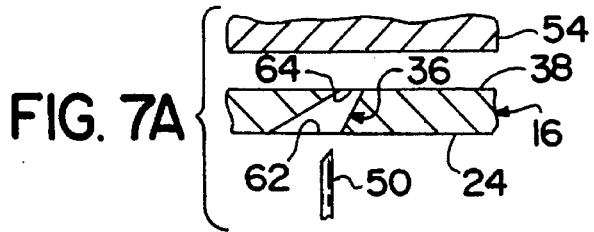
FIGS. 7A and 7B are fragmentary cross-sectional views of an aperture for shaping tissue engaging members of a surgical clip according to the present invention.
Figure 7B:
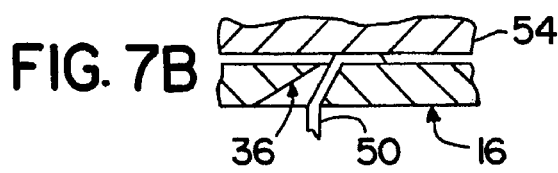

A modification of the ligating clip of the present invention is shown in FIG. 7A, wherein the modified ligating clip has an upper arm 16 similar to that previously described but with generally conical apertures 36 defining large openings 62 along the inner face 24 of upper arm 16 and tapering to relatively smaller openings 64 along the outer face 38 of upper arm 16. The apertures 36 making up a given pair 28, 30, 32 or 34 are tilted toward or away from one another to form angled camming surfaces for bending the tissue penetrating legs 50 of a staple 40 as the legs pass through the apertures as shown in FIG. 7B.

Figure 8:
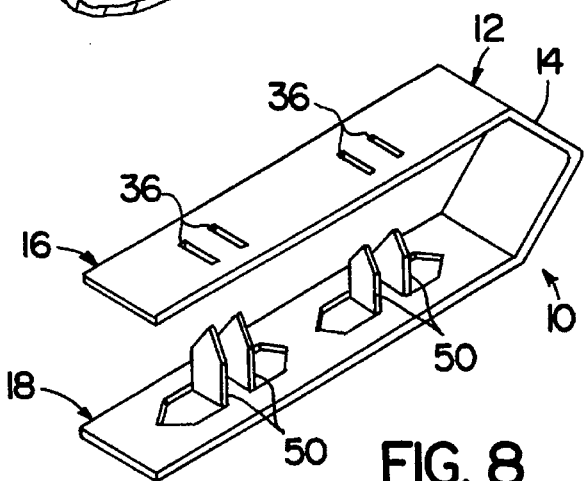
FIG. 8 is a perspective view of a modified surgical clip according to the present invention.

Another modification of the ligating clip 10 of the present invention is shown in FIG. 8 with the primary difference being that the deformable strip 12 and tissue penetrating legs 50 are formed as an integral, one-piece construction. The strip 12 can thus be stamped from a single sheet of ductile bioabsorbable or non-bioabsorbable medical grade material to form a plurality of sharp tabs that can be folded away from the lower arm 18 as shown to form the tissue penetrating legs 50. Apertures 36 are formed in upper arm 16 in opposed relation to the integrally formed tissue penetrating legs 50 and are configured to allow passage of the legs therethrough when opposed arms 16 and 18 are closed together.

Figure 9:
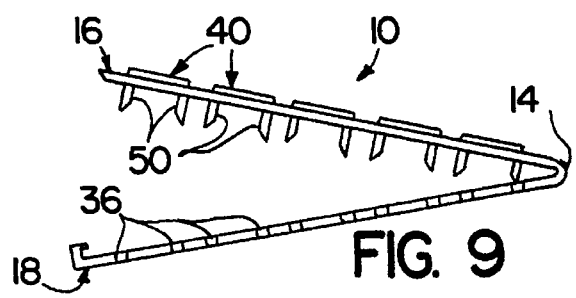
FIG. 9 is a side view of another modified surgical clip according to the present invention.

FIG. 9 illustrates yet another modification of the surgical clip of the present invention wherein the staples 40 are mounted on the upper arm 16 in opposition to apertures 36 formed in the lower arm 18 and the base 14 is an acutely angled bend or fold from which the arms 16 and 18 divergingly extend when open.

Figure 10:
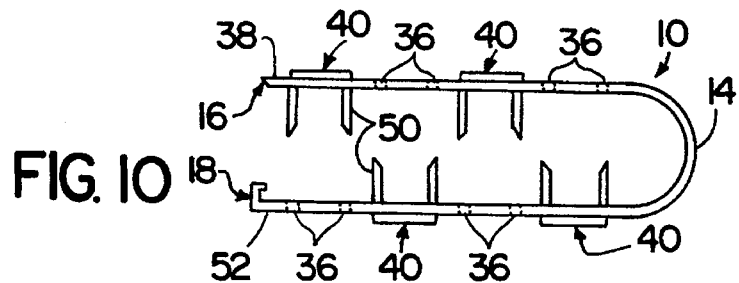
FIG. 10 is a side view of yet another modified surgical clip according to the present invention.

The modified surgical clip shown in FIG. 10 is similar to those previously described but with a rounded or semicircular base 14 and staples 40 mounted on both the upper and lower arms 16 and 18 with tissue penetrating legs 50 positioned opposite apertures 36 formed in the other arm. When applied to anatomical tissue in the manner described above, the clip shown in FIG. 10 will have plastically shaped or deformed legs bearing against the outer faces 38 and 52 of both the upper and lower arms providing visual confirmation from either side that the clip has been properly applied.

Figure 11:
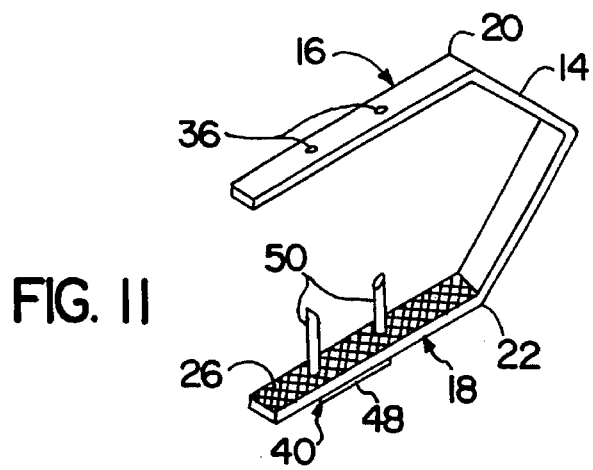
FIG. 11 is a perspective view of still another modified surgical clip according to the present invention.

Still another modification of the surgical clip of the present invention is illustrated in FIG. 11. The modified clip is similar to the clip shown in FIG. 1 with the exception that lower arm 18 carries a single staple 40 having a pair of tissue penetrating legs 50 aligned with apertures 36 formed in the upper arm 16. Accordingly, arms 16 and 18 can be made shorter and the length of the clip minimized for procedures where space is limited and/or small tubular organs and vessels are to be constricted. The inner face 26 of the lower arm 18 is also shown having a knurled configuration or tread for gripping an occluded organ or vessel when the arms of the clip are clamped together; and it will be appreciated that a similar tissue gripping surface can be formed on the inner face 24 of upper arm 16 in opposed relation to the knurled surface shown for gripping organs and vessels from both sides. Arms 16 and 18 of the modified clip also differ from those shown in FIG. 1 in that neither arm is configured to mate at a distal end with the other arm; and, accordingly, the arms 16 and 18 are held together primarily because of the ductile nature of the clip and of the tissue penetrating members engaging the arms of the clip.

Figure 12:
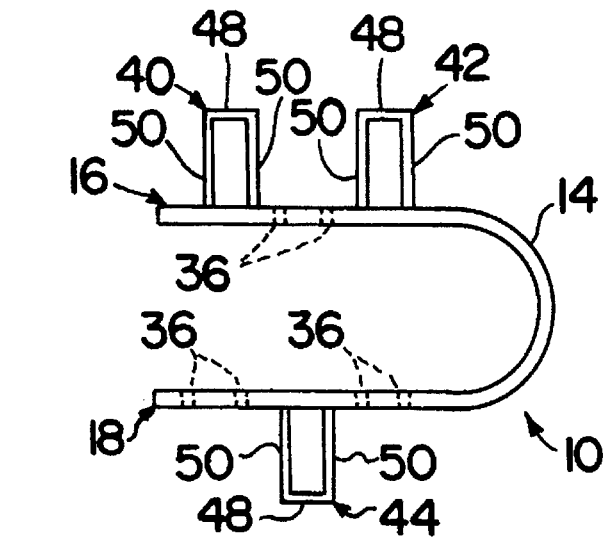
FIG. 12 is a side view of a modified surgical clip according to the present invention.

FIG. 12 illustrates another modification of the surgical clip of the present invention wherein the staples 40, 42 and 44 are mounted on both the upper and lower arms 16 and 18 with tissue penetrating legs 50 retracted or withdrawn into the arms so that the sharp tissue penetrating tips of the legs are not exposed prior to compression of the clip. Upper arm 16 is shown carrying two staples 40 and 42 with tissue penetrating legs 50 aligned with apertures 36 in lower arm 18 and cross-members 48 elevated above the upper arm. Lower arm 18 is shown carrying a single staple 44 with tissue penetrating legs 50 aligned with apertures 36 in upper arm 16 and a cross-member 48 spaced below the lower arm looking at FIG. 12. Neither arm is configured to mate at a distal end with the other arm.

Figure 13:
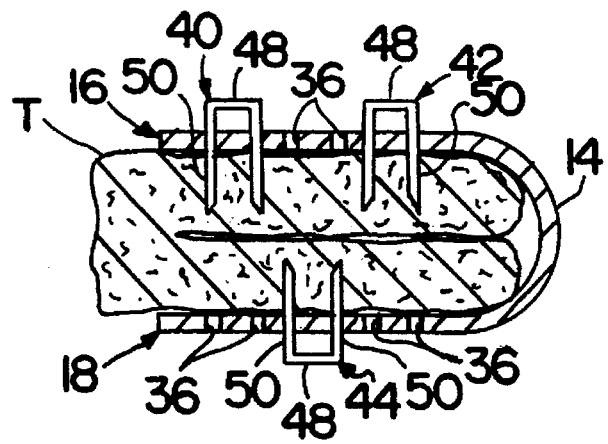
FIGS. 13–15 are side views, partly in section, illustrating use of the surgical clip of FIG. 12.
Figure 14:
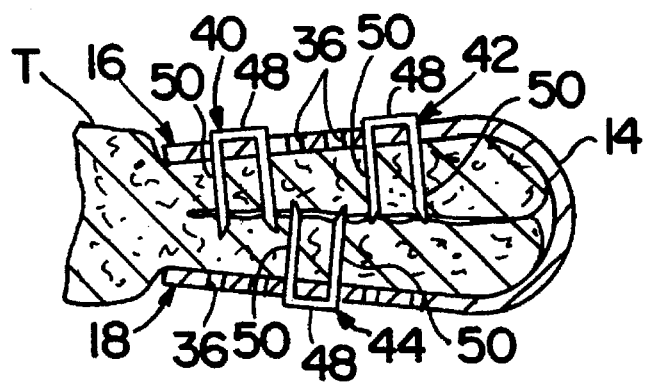
Figure 15:
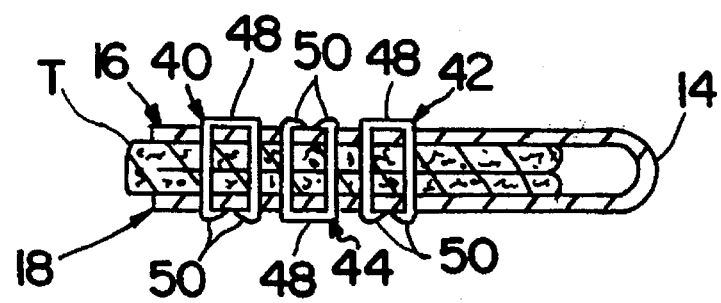

Use of the surgical clip of FIG. 12 for occluding anatomical tissue is illustrated in FIGS. 13–15. The tissue T is positioned between arms 16 and 18 of the clip with staple legs 50 retracted into the arms as shown in FIG. 12, and the clip 10 is compressed. Since cross-members 48 stick out from arms 16 and 18, compression of the clip causes the tissue penetrating legs 50 to be driven through openings in the arms and into the tissue T as shown in FIG. 13. Further compression causes the cross-members 48 to abut respective outer surfaces of arms 16 and 18 as the arms are moved toward one another against the tissue T as shown in FIG. 14. When the arms 16 and 18 are separated by a distance somewhat less than the length of the tissue penetrating legs 50, the legs 50 pass through apertures 36 in the opposed arm and are bent around the other side as illustrated in FIG. 15 to lock the arms together without distal ends of the arms being coupled. This is particularly advantageous where only a portion of a vessel or organ is to be occluded and, therefore, the distal ends of the arms will be separated by tissue when the clip is applied.

Figure 16:
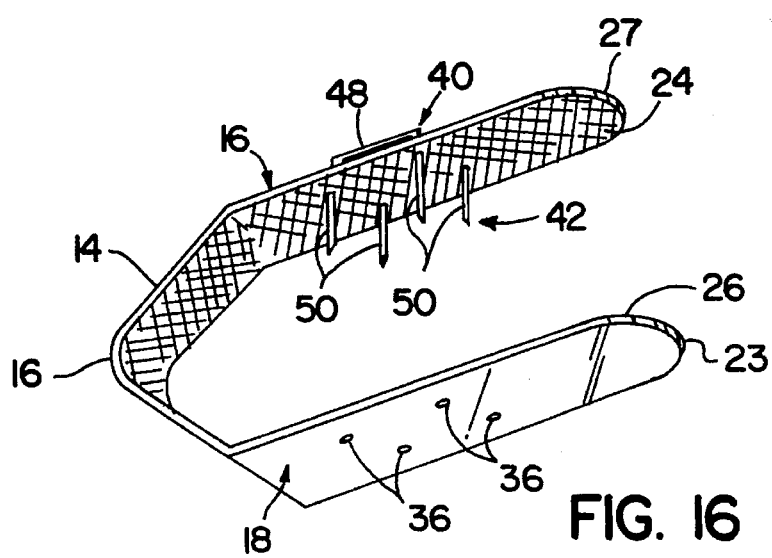
FIG. 16 is a perspective view of yet another modified clip according to the present invention.

Another modification of the surgical clip of the present invention is shown in FIG. 16 wherein a pair of staples 40 and 42 are mounted on the upper arm 16 of the clip with tissue penetrating legs 50 arranged in parallel rows opposite apertures 36 in the lower arm 18. Staple cross members 48 in each row are staggered or longitudinally offset from one another so that the staples 40 and 42 are only partly coextensive. Also in FIG. 16, inside surfaces 24 and 26 of the arms and the inside surface of the base 14 are provided with a textured or knurled tread for improved gripping along the length of the clip. In addition, base 14 includes a rounded apex 62 and distal ends 27 and 23 of the upper and lower arms 16 and 18 form rounded edges to prevent injury to tissue and organs within an anatomical cavity.

Figure 17:
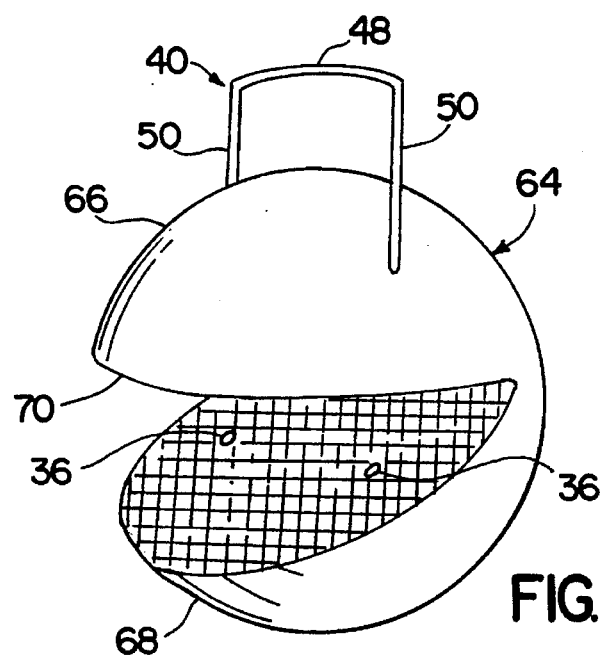
FIG. 17 is a perspective view of another modified clip according to the present invention.

The modified surgical clip illustrated in FIG. 17 includes a spherical body 64 separated into upper and lower hemispherical arms 66 and 68 by a wedge-shaped cutout 70. A staple 40 is mounted on the upper hemispherical arm 66 and includes an arcuate cross member 48 elevated above the upper hemispherical arm and a pair of tissue penetrating legs 50 extending through the arm in opposed relation to apertures 36 formed through the lower hemispherical arm 68.

In use, the surgical clip of FIG. 17 is held between jaws of a forceps or a suitable clip applier and the object or tissue to be clamped is positioned within the wedge-shaped cutout 70 between the hemispherical arms 66 and 68. The spherical body 64 is then compressed using the forceps or clip applier so that the hemispherical arms move toward one another on opposite sides of the object or tissue to grip the object or tissue which is positioned within the wedge-shaped cutout. At the same time, staple legs 50 are driven through the upper hemispherical arm 66 and into apertures 36 until they protrude from the bottom of the lower hemispherical arm 68 and are bent to lock the arms together and to provide visual confirmation that the clip has been properly applied.

From the above, it will be appreciated that the present invention prevents loosening of a surgical clip having opposed arms clamped around an anatomical vessel or organ and applies a more uniform pressure across the occluded vessel or organ by use of ductile tissue penetrating members that pass through apertures in at least one of the arms and are bent or plastically deformed against that arm. The present invention is also advantageous in that the bent tissue penetrating members provide a visual confirmation that the clip has been properly applied. The tissue penetrating members can be integrally formed as part of the surgical clip or can be the legs of staples carried by one or both arms of the clip. In either case, any number of rows of tissue penetrating members can be utilized and the number of tissue penetrating members per row can be varied according the size of the clip and the vessel or organ to be occluded. If multiple rows of tissue penetrating members are carried by one or both arms of the clip, the tissue penetrating members in adjacent rows can be longitudinally aligned or staggered as desired. Furthermore, tissue penetrating members can be carried on one side of the base opposite apertures in the other side of the base as shown in phantom at 50 in FIG. 1. In order to facilitate bending of the tissue penetrating legs after passing through apertures in one of the arms, the legs and/or apertures can be canted away from one another or toward one another to present angled or curved surfaces facilitating deformation of the legs.

The base and arms of the present invention can have any configuration in cross-section, including polygonal, circular and elliptical configurations, but preferably resemble in overall shape and size conventional surgical clips of the type which can be applied using commonly available clip applying instruments. Tissue gripping surfaces, such as the knurled tread shown at 26 in FIG. 11, can be formed on any portion of the base and/or arms of the clips to improve engagement of the clips with the vessels and organs they occlude. Furthermore, any number of flattened regions and/or recesses can be formed on the base and/or arms of the clips for performing various tissue engaging and/or staple receiving functions.

The clips can be applied to tissue individually from between jaws, such as by use of a forceps adapted to hold the clips, or multiple clips can be loaded in a clip applier and advanced individually between the jaws. Also, multiple clips can be applied simultaneously if advanced into plural spaced grooves formed in opposed jaws of a clip applier, and if multiple clips are applied simultaneously, a cutting member such as a blade can be advanced between the clips after they have been applied in order to transect the tissue between the clips.

The clip of the present invention has been described herein as being useful for constricting anatomical tissue such as vessels and organs. It will be appreciated, however, that the clip can be used to clamp, clinch, compress, constrict or pinch any type of object or structure during medical procedures. The clip can also function as a knot to hold ends of suture material together.

Opposed distal ends of the arms of the surgical clip can be configured to couple when closed or merely to contact or move toward one another. If configured to couple, any latch or hooking mechanism can be used, including the latching configurations shown and described in U.S. Pat. No. 5,100,418, to Yoon et al, which is incorporated herein by reference.

The features of the various embodiments described above can be combined in any manner desired dependent upon the procedure to be performed and the method of applying the clip.

Inasmuch as the present invention is subject to many variations, modifications and changes in detail, it is intended that all subject matter discussed above are shown in the accompanying drawings be interpreted as illustrative only and not be taken in a limiting sense.

What is claimed is:

1. A surgical clip comprising a base and at least two generally opposed arms extending from said base;

an aperture formed in a first of said arms; and a ductile tissue penetrating member carried by a second of said arms in opposed relation to said aperture;

said ductile tissue penetrating member having a length to pass through said aperture and be bent against said first arm when said arms are moved toward one another.

2. A surgical clip as recited in claim 1 and further comprising a plurality of apertures formed in said first arm and a plurality of ductile tissue penetrating members carried by said second arm in opposed relation to said apertures.

3. A surgical clip as recited in claim 2 wherein said tissue penetrating members are formed by at least one staple having ductile tissue penetrating legs inserted through openings formed in said second arm.

4. A surgical clip as recited in claim 3 and further comprising a plurality of staples having ductile tissue penetrating legs inserted through openings formed in said second arm.

5. A surgical clip as recited in claim 2 wherein said apertures and tissue penetrating members are colinearly arranged along a longitudinal axis of said surgical clip.

6. A surgical clip as recited in claim 1 wherein said tissue penetrating member is integrally formed as a unitary part of said second arm.

7. A surgical clip as recited in claim 1 and further comprising a plurality of apertures formed in each arm and a plurality of ductile tissue penetrating members carried by each arm in opposition to said apertures formed in the other of said arms.

8. A surgical clip as recited in claim 1 wherein one of said arms includes coupling means at a distal end for receiving the distal end of the other of said arms.

9. A surgical clip as recited in claim 1 wherein said base is V-shaped and said arms extend from opposite ends of said V-shaped base in substantially parallel orientation relative to one another.

10. A surgical clip as recited in claim 1 wherein said base is curved and said arms extend from opposite ends of said curved base.

11. A surgical clip as recited in claim 1 wherein said base is acutely angled and said arms diverge from opposite ends of said base.

12. A surgical clip as recited in claim 1 wherein said aperture includes camming means for bending said tissue penetrating member as it passes through said aperture.

13. A surgical clip as recited in claim 1 wherein said base and said arms are formed of a ductile material.

14. A method of constricting anatomical tissue comprising the steps of positioning the anatomical tissue between generally opposed arms of a ductile clip;

compressing the clip around the anatomical tissue;

penetrating through the anatomical tissue with ductile tissue penetrating members carried by at least one of the arms;

passing ends of the tissue penetrating members through apertures in the other arm until they protrude; and bending the protruding ends of the tissue penetrating members against the other arm.

15. A method of constricting anatomical tissue as recited in claim 14 wherein the step of compressing the clip includes bending the ductile clip to move distal ends of the arms together and further comprising the step of coupling the distal ends together.

16. A surgical clip comprising a base and at least two generally opposed arms extending from said base;

a plurality of apertures formed in a first of said arms; and a plurality of ductile tissue penetrating members carried by a second of said arms in opposed relation to said apertures:

wherein said apertures include camming means for bending said tissue penetrating members as they pass through said apertures.

* * * * *